United States Patent
Moran, Jr. et al.

(10) Patent No.: US 7,307,718 B2
(45) Date of Patent: Dec. 11, 2007

(54) DETERMINING AN ANALYTE BY MULTIPLE MEASUREMENTS THROUGH A CUVETTE

(75) Inventors: Donald James Moran, Jr., Rochester, NY (US); Michael W. LaCourt, Spencerport, NY (US); Davis Freeman, III, Rochester, NY (US); Merrit Jacobs, Fairport, NY (US); David Allen Heavner, Fairport, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 161 days.

(21) Appl. No.: 11/047,450

(22) Filed: Jan. 31, 2005

(65) Prior Publication Data

US 2005/0185177 A1    Aug. 25, 2005

Related U.S. Application Data

(63) Continuation-in-part of application No. 10/784,505, filed on Feb. 23, 2004, now abandoned.

(51) Int. Cl.
  *G01J 3/42* (2006.01)
  *G01N 21/64* (2006.01)
(52) U.S. Cl. ............... 356/300; 356/319; 356/326; 356/317; 250/458.1
(58) Field of Classification Search ............ 356/300, 356/319, 323, 325, 326, 328, 436, 317, 318, 356/417; 250/458.1, 459.1, 461.1
See application file for complete search history.

(56) References Cited

U.S. PATENT DOCUMENTS 3,355,856 A    12/1967   Randrup 3,544,272 A    12/1970   Vaills (Continued)

FOREIGN PATENT DOCUMENTS

CA        2019511        9/1994

(Continued)

OTHER PUBLICATIONS

Clin. Chem., vol. 38, pp. 1623-1631, 1992.

(Continued)

*Primary Examiner*—F. L. Evans
(74) *Attorney, Agent, or Firm*—Todd J. Burns

(57) ABSTRACT

A method for measuring the presence or concentration of an analyte in a sample by spectrophotometry: providing an open top cuvette having a sample with an analyte to be measured; providing a light source and a detector for detecting emitted light; taking at least two measurements that includes: (i) directing at least two beams of light from the light source to different locations on the cuvette; (ii) passing the at least two beams through the cuvette at their respective locations and through the sample to be measured; and (iii) measuring at least two respective emitted light beams with the detector; and comparing the at least two emitted light beams to determine if: all the emitted light beams should be disregarded; one or more of the emitted light beams should be disregarded; or the sample absorbances should be averaged. In a preferred embodiment, the method includes taking at least three measurements. In another preferred embodiment, the spectrophotometry is absorption spectrophotometry, and the method is performed on a diagnostic analyzer.

30 Claims, 12 Drawing Sheets

U.S. PATENT DOCUMENTS

| | | |
|---|---|---|
| 3,754,872 A | 8/1973 | Zauft |
| 3,897,216 A | 7/1975 | Jones |
| 4,066,365 A | 1/1978 | Staunton |
| 4,123,173 A | 10/1978 | Bullock et al. |
| 4,208,127 A | 6/1980 | Hufenreuter |
| RE30,391 E | 9/1980 | Liston |
| 4,431,307 A | 2/1984 | Suovaniemi |
| 4,468,371 A | 8/1984 | Chen et al. |
| 4,496,293 A | 1/1985 | Nakamura et al. |
| 4,517,160 A | 5/1985 | Galle et al. |
| 4,517,851 A | 5/1985 | Tice |
| 4,549,809 A | 10/1985 | Minekane et al. |
| 4,595,562 A | 6/1986 | Liston et al. |
| 4,614,434 A | 9/1986 | Welch et al. |
| 4,629,703 A | 12/1986 | Uffenheimer |
| 4,636,477 A | 1/1987 | Rönka et al. |
| 4,639,135 A | 1/1987 | Borer et al. |
| 4,648,712 A | 3/1987 | Brenholdt |
| 4,666,853 A | 5/1987 | Meserol et al. |
| D290,170 S | 6/1987 | Käyhkö |
| 4,682,890 A | 7/1987 | De Macario et al. |
| 4,741,429 A | 5/1988 | Hattori et al. |
| 4,743,561 A | 5/1988 | Shaffar |
| 4,797,000 A * | 1/1989 | Curtis ............... 356/436 |
| 4,950,077 A | 8/1990 | Manabe |
| 5,064,282 A | 11/1991 | Curtis |
| 5,092,342 A * | 3/1992 | Hattendorff et al. ........ 600/532 |
| 5,255,514 A | 10/1993 | Wentworth, Jr. |
| 5,273,715 A | 12/1993 | Bridgham et al. |
| 5,309,216 A | 5/1994 | Weichert |
| 5,314,825 A | 5/1994 | Weyrauch et al. |
| 5,353,910 A | 10/1994 | Harris et al. |
| 5,360,597 A | 11/1994 | Jakubowicz et al. |
| 5,380,666 A | 1/1995 | Wuerschum |
| 5,402,240 A | 3/1995 | Thistlethwaite et al. |
| 5,432,096 A | 7/1995 | Zhu |
| 5,482,839 A | 1/1996 | Ashihara et al. |
| 5,525,514 A | 6/1996 | Jacobs et al. |
| 5,535,744 A | 7/1996 | DiNino |
| 5,599,501 A | 2/1997 | Carey et al. |
| 5,729,342 A | 3/1998 | Yokoyama et al. |
| 5,735,378 A | 4/1998 | Sundquist |
| 5,764,354 A | 6/1998 | Aidam |
| 5,774,209 A | 6/1998 | Shestock |
| 5,849,247 A | 12/1998 | Uzan et al. |
| 5,853,666 A | 12/1998 | Seaton et al. |
| 5,900,557 A | 5/1999 | Tanihata et al. |
| 5,944,477 A | 8/1999 | Shill |
| 6,047,082 A | 4/2000 | Rhody et al. |
| 6,081,326 A | 6/2000 | Rousseau et al. |
| 6,196,375 B1 | 3/2001 | Cozza |
| 6,274,872 B1 | 8/2001 | Katerkamp |
| 6,328,164 B1 | 12/2001 | Rickkinen et al. |
| 6,358,471 B1 | 3/2002 | Ishihara |
| 6,374,987 B1 | 4/2002 | Heuft et al. |
| 6,388,751 B1 * | 5/2002 | Holley ............... 356/436 |
| 6,451,259 B1 | 9/2002 | Cohen et al. |
| 2002/0169368 A1 | 11/2002 | Hwang et al. |
| 2003/0003591 A1 | 1/2003 | LaCourt et al. |
| 2003/0022380 A1 | 1/2003 | Jakubowicz et al. |
| 2003/0026733 A1 | 2/2003 | LaCourt et al. |
| 2003/0104634 A1 | 6/2003 | Jacobs et al. |
| 2003/0128363 A1 | 7/2003 | Aberle et al. |
| 2003/0137650 A1 | 7/2003 | Fine et al. |
| 2003/0147078 A1 | 8/2003 | Zirk et al. |
| 2005/0014284 A1 | 1/2005 | Jacobs et al. |
| 2005/0078307 A1 | 4/2005 | Freeman, III et al. |
| 2005/0185177 A1 | 8/2005 | Moran, Jr. |

FOREIGN PATENT DOCUMENTS

| | | |
|---|---|---|
| EP | 0953843 | 11/1999 |
| WO | WO 2004/027375 | 4/2004 |

OTHER PUBLICATIONS

Anal. Chem., vol. 59, No. 17, pp. 1007A-1017A, Sep. 1987.
Anal. Chem., vol. 66, No. 15, pp. 795A-804A, Aug. 1994.
Shimadzu Corp., Patent Abstracts of Japan, vol. 2003, No. 7, Jul. 3, 2003.
Matsushita Electric Ind. Co. LTD., Patent Abstracts of Japan, vol. 2000, No. 6, Sep. 22, 2000.
Mitsubishi Electric Corp., Patent Abstracts of Japan, vol. 6, No. 192 (P-145), Sep. 30, 1982.
Hitachi LTD., Patent Abstracts of Japan, vol. 12, No. 401 (P-776), Oct. 25, 1988.

* cited by examiner

Passing Patterns for Decision Block 5

Failing Patterns for Decision Block 5

Passing Patterns for Decision Block 8

Failing Patterns for Decision Block 8

Passing Patterns for Decision Block 10

Failing Patterns for Decision Block 10

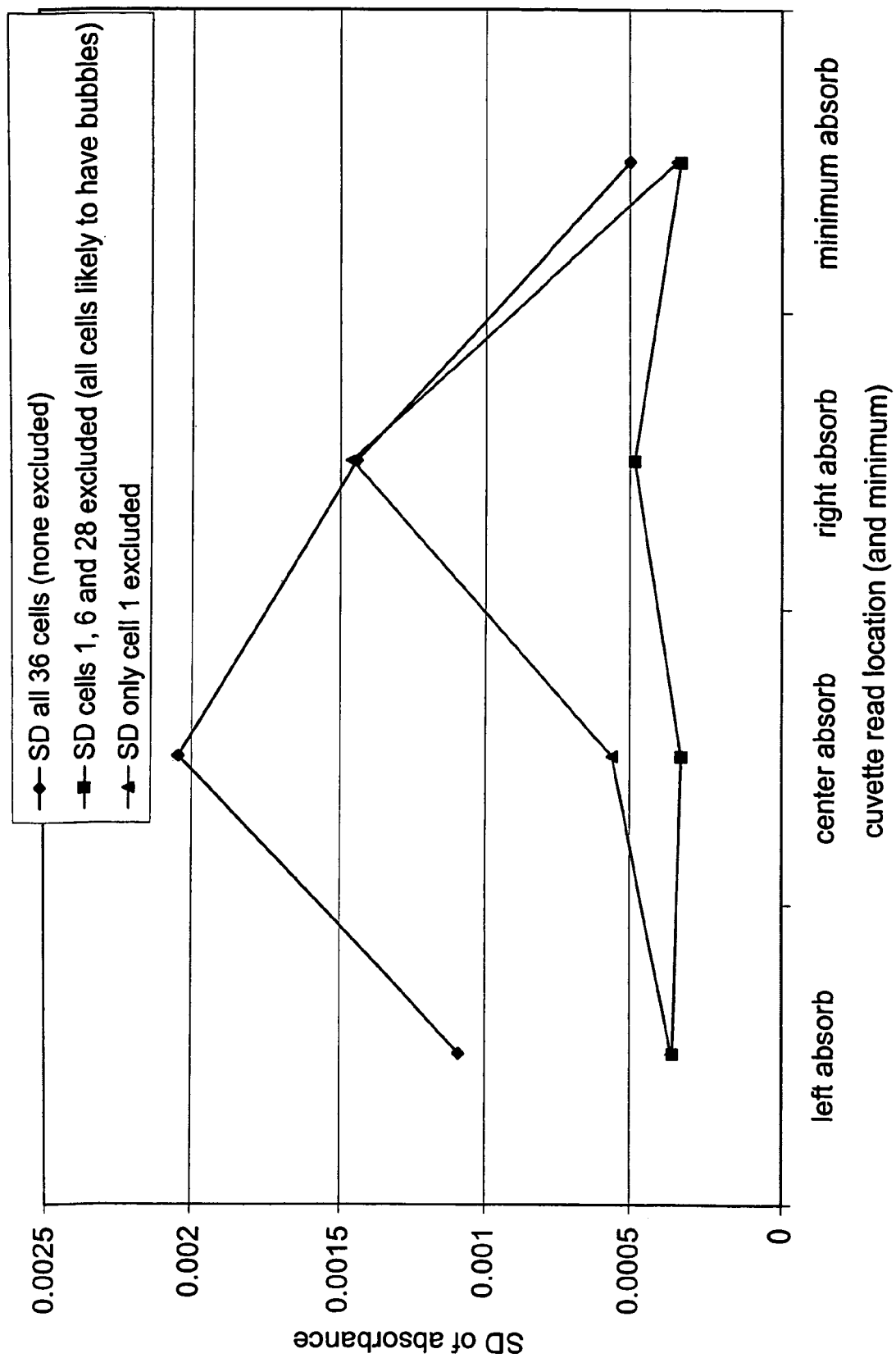

DETERMINING AN ANALYTE BY MULTIPLE MEASUREMENTS THROUGH A CUVETTE

CROSS REFERENCE TO RELATED APPLICATIONS

This application claims priority as a continuation-in-part to Ser. No. 10/784,505, filed Feb. 23, 2004, now abandoned the contents of which are incorporated herein by reference in its entirety.

BACKGROUND OF THE INVENTION

The present invention relates to measuring the presence or concentration of an analyte in a sample, particularly by spectrophotometry on a diagnostic analyzer. In particular, the present invention relates to reducing the number of rejects or re-runs in measuring the concentration of an analyte in a sample by taking multiple measurements through the cuvette containing the sample and reagent.

Known diagnostic assays and other analysis that use cuvettes as the reaction chamber or container for taking measurements often have problems with imprecise results associated with measurements of emitted light, such as absorbance measurements, that are influenced by interfering objects in the measurement path. These interfering objects, which can be transient or non-transient, can include any number of things from dirt or dust in the cuvette, dirt or dust on the exterior of the cuvette window, fingerprints on the surface of the cuvettes and air bubbles in the fluid. In addition to interfering objects, measurement error and therefore imprecision of diagnostic assays performed in a cuvette can be influenced by measuring a fluid, e.g., sample, that was not homogeneously mixed (chemically or thermally). The problems of interfering objects can be exacerbated by open top cuvettes which are open to receiving fluids (e.g., sample and/or reagents) from a dispensing or aspirating pipette or proboscis and are thus open to the introduction of dirt from the ambient environment and additional bubbles from the dispense of fluid into the cuvette. The present inventors have found that these transient conditions can be substantial contributors to assay imprecision which often leads to the assay being rejected, thus resulting in the time consuming and costly reanalysis (re-running) of samples. Some of these factors can be reduced by controlling the analysis process. For example, mixing within the cuvette can be improved as disclosed in pending application Ser. No. 10/622,258 filed Jul. 18, 2003 entitled "Improved Fluid Mixing." Cuvette loading can be improved to reduce dirt and fingerprints as disclosed in pending application Ser. No. 10/684,536 filed Oct. 14, 2003 entitled "Packaging Of Multiple Fluid Receptacles."

A more difficult problem to eliminate or reduce is the formation of air bubbles in the fluid. The bubbles can be introduced by air being mixed in during sample or reagent dispense. Alternatively, air bubbles can be formed in the fluid because the fluid has more dissolved air present when it is cold than when it is warm, and the reagents, which are stored cold, are warmed up in the cuvettes. As a result, bubbles of air tend to form on the surfaces of the cuvette as the reagents are warmed. If they are located in the measurement window part of the cuvette they may cause substantial error in the measurement and ultimately in the determination of the assay concentration.

U.S. Pat. No. 4,123,173 discloses a rotatable flexible cuvette array. U.S. Pat. No. 4,648,712 discloses a method for determining the basis weight of a fibrous web that includes reading multiple areas of web. U.S. Pat. No. 4,549,809 discloses curved cuvettes and taking multiple readings to determine the position of the cuvette and using a single measurement for analysis. U.S. Pat. No. 5,402,240 discloses a sperm densimeter that takes a plurality of sample transmission measurements and calculates an average based on the plurality of measurements. U.S. Pat. No. 5,535,744 discloses an analysis method that includes multiple reads for each cuvette which are averaged to determine a final result. U.S. Pat. No. 5,255,514 discloses a method for determining wash effectiveness on a dry slide test element that includes reading at different locations on the slide. U.S. Pat. No. 5,853,666 discloses a sealed test card having a plurality of wells containing sample to be analyzed by fluorescence. Measurements are taken at multiple positions across the well to detect any air pockets or debris and to detect and reject abnormal transmittance measurements.

None of the known art described above, adequately addresses resolving the problems described above, in particular, of improving precision of measurements through a cuvette to reduce or even eliminate the number of re-runs that have to be performed on a sample, in particular, by detecting and reducing or eliminating errors in reading through a cuvette. For the foregoing reasons, there is a need for a method of improving precision, more particularly detecting and reducing or eliminating errors during measurement of an analyte by spectrophotometry.

SUMMARY OF THE INVENTION

The present invention is directed to a method that solves the foregoing problems of improving precision, in particular in detecting and eliminating or reducing errors to reduce the number of samples that have to be re-run and hence the time and cost of analysis. In some embodiments, the present invention also results in improvement in the accuracy of results. One aspect of the invention is directed to a method for measuring the presence or concentration of an analyte in a sample by spectrophotometry, which includes: providing an open top cuvette having a sample with an analyte to be measured; providing a light source and a detector for detecting emitted light; taking at least two measurements that includes: (i) directing at least two beams of light from the light source to different locations on the cuvette; (ii) passing the at least two beams through the cuvette at their respective locations and through the sample to be measured; and (iii) measuring at least two respective emitted light beams with the detector; and comparing the at least two emitted light beams to determine if: all the emitted light beams should be disregarded; one or more of the emitted light beams should be disregarded; or the sample absorbances should be averaged. In a preferred embodiment, the method includes taking at least three measurements and comparing the at least three emitted light beams to determine if: all the emitted light beams should be disregarded; one or more of the emitted light beams should be disregarded; or the emitted light beams should be averaged. In another preferred embodiment, the spectrophotometry is absorption spectrophotometry.

In a preferred embodiment, prior to the step of directing at least two beams, the method further includes: (i) directing at least two beams of light from the light source at their respective different locations on the cuvette; (ii) passing the at least two beams through the cuvette alone or the cuvette and sample before the sample has reacted with reagents; and (iii) measuring at least two respective blank absorbances from the emitted light corresponding to the at least two beams with the detector; and selecting at least one blank absorbance; and subtracting at least one blank absorbance from the at least two sample absorbances to result in corrected sample absorbances. In a preferred embodiment, the analysis is performed on a diagnostic analyzer and the light has a wavelength in the range of 300 to 1100 nm.

According to another aspect of the invention there has been provided a method for measuring the presence or concentration of an analyte in a sample by absorption spectrophotometry, which includes: providing a cuvette having a sample with an analyte to be measured; providing a source of light and a detector for detecting the light; taking at least three measurements that includes: (i) directing at least three beams of the light to different locations on the cuvette; (ii) passing the at least three beams through the cuvette at their respective locations and through the sample to be measured; and (iii) measuring at least three respective sample absorbances of the transmitted beams with the detector; and comparing the at least three sample absorbances to determine if: all the sample absorbances should be disregarded; one or more of the sample absorbances should be disregarded and the remaining absorbances retained; or all the sample absorbances should be averaged, wherein: if at least two sample absorbances are retained and an average retained absorbance is less than a first selected absorbance then the lowest absorbance is used in determining the presence or concentration of the analyte; or if at least two sample absorbances are retained and an average retained absorbance is greater than or equal to a second selected absorbance then the highest absorbance is used in determining the presence or concentration of the analyte.

According to yet another aspect of the invention, there has been provided a method for measuring the presence or concentration of an analyte in a sample by absorption spectrophotometry. The method includes: (A) providing a cuvette having a sample with an analyte to be measured; (B) providing a source of light and a detector for detecting the light; (C) taking at least three measurements that includes: (i) directing at least three beams of the light to different locations a, b and c on the cuvette; (ii) passing the at least three beams through the cuvette at their respective locations a, b and c and through the sample to be measured; and (iii) measuring at least three respective sample absorbances Aa, Ab and Ac of the transmitted beams with the detector; (D) determining the absolute value of the difference between each pair of absorbances to arrive at |Aa−Ab|, |Ac−Ab| and |Ac−Aa|; (E) comparing an absolute value of the difference between each pair of absorbances with a predetermined limit; (F) if one or more of each the absolute value of the difference is ≧ the predetermined limit, then compare each absorbance to a predetermined absorbance: (i) if one or more absorbances are above the predetermined absorbance, then disregard all readings and proceed to step (K); or (ii) if all absorbances are below the predetermined absorbance, then (G) determine the smallest absolute value of the difference between each pair of absorbances; (H) determine if the smallest absolute value of the difference is < a predetermined fraction of the predetermined limit: (i) if the smallest absolute value of the difference is not less than the predetermined fraction of the limit then disregard all readings and proceed to step (K); or (ii) if the smallest absolute value of the difference is less than the predetermined fraction of the limit, then (I) determine which of the absolute value of the difference between each pair of absorbances is the smallest absolute value of difference; (J) determine which absorbance in the smallest absolute value should be selected or if the results should be disregarded; and (K) either re-evaluating the analysis if the results should be disregarded in steps (F), (H) or (J), or calculating the presence concentration of the analyte in the sample by using the selected absorbance.

In a preferred embodiment, in the method described above, prior to the step of directing at least three beams, the method further includes: (i) directing at least three beams of the light at their respective different locations a, b and c on the cuvette; (ii) passing the at least three beams through the cuvette alone or the cuvette and sample before the sample has reacted with reagents; (iii) measuring at least three respective blank absorbances A1a, A1b and A1c of the transmitted beams with the detector; (iv) determining the sample absorbance Aa, Ab, and Ac by subtracting the blank absorbance A1a, A1b and A1c from measured sample absorbance A2a, A2b and A2c, respectively; wherein the step of determining which read in the smallest absolute value of the difference between each pair of absorbances should be selected or if the results should be disregarded (J) comprises: (J1) if the smallest absolute value of the difference between each pair of absorbances is |(A2a−A1a)−(A2b−A1b)|, then if A1c+A2c is greater than each of A1a+A2a and A1b+A2b, compare A1a+A2a and A1b+A2b, if A1a+A2a<A1b+A2b then absorbance Aa is the selected absorbance, otherwise absorbance Ab is the selected absorbance, if A1c+A2c is ≦ to one of A1a+A2a and A1b+A2b, then disregard all readings and proceed to step (K); (J2) if the smallest absolute Value of the difference between each pair of absorbances is |(A2c−A1c)−(A2b−A1b)|, then if A1a+A2a is greater than each of A1b+A2b and A1c+A2c, compare A1c+A2c and A1b+A2b, if A1c+A2c<A1b+A2b then absorbance Ac is the selected absorbance, otherwise-absorbance Ab is the selected absorbance, if A1a+A2a is ≦ to one of A1b+A2b and A1c+A2c, then disregard all readings and proceed to step (K); or (J3) if the smallest absolute value of the difference between each pair of absorbances is |(A2c−A1c)−(A2a−A1a)|, then if A1b+A2b is greater than each of A1a+A2a and A1c+A2c, compare A1c+A2c and A1a+A2a, if A1c+A2c<A1a+A2a then absorbance Ac is the selected absorbance, otherwise absorbance Aa is the selected absorbance, if A1b+A2b is ≦ to one of A1a+A2a and A1c+A2c, then disregard all readings and proceed to step (K).

According to another aspect of the invention, the method described above is implemented by a computer program interfacing with a computer. Another aspect of the invention provides an article of manufacture comprising a computer usable medium having computer readable program code configured to conduct the method described above.

Further objects, features and advantages of the present invention will be apparent to those skilled in the art from detailed consideration of the preferred embodiments that follow.

BRIEF DESCRIPTION OF THE DRAWINGS

FIG. 10 is a graph showing the standard deviation of absorbance at three different locations on the cuvettes and the minimum absorbance on each cuvette using three different threshold discards for the measurements shown in FIG. 9.

DETAILED DESCRIPTION OF PREFERRED EMBODIMENTS

Figure 1:
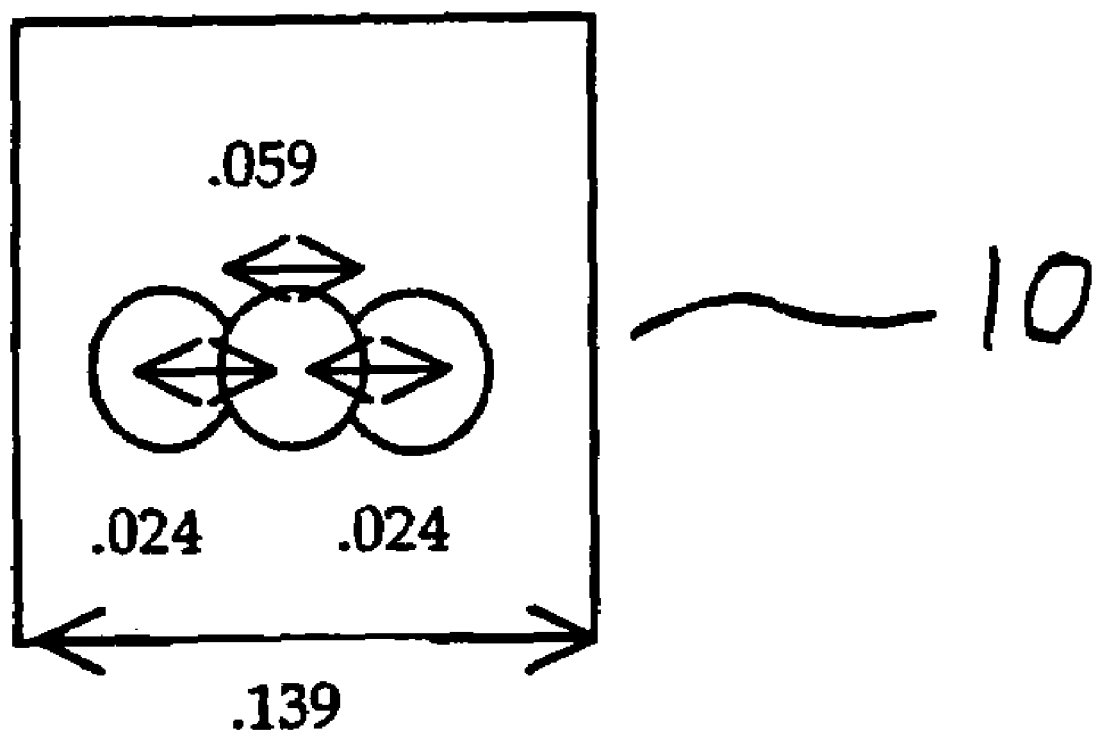
FIG. 1 is a schematic diagram showing one embodiment of the measurement window of a cuvette with three measurements at different locations on the window.

The present invention includes a method for measuring an analyte in a sample by spectrophotometry, including a method for detecting one or more errors during the measurement of a sample and then applying an appropriate correction if an error is detected. Broadly, the method involves providing a light source which directs a beam of light from the light source (defined below) through the sample to be measured at least two different locations in the cuvette, containing the sample, and measuring the amount of light emitted from the cuvette and sample. The measurements are compared with one another. Based upon the comparison, in particular the difference in the measurements of emitted light of these samples, one can determine whether there has been: an error in one or more of the measurements and take appropriate action, such as discarding or disregarding one or more of the measurements as an outlier and using the remaining measurements for the analysis, or alternatively disregarding all measurements and either remeasuring the sample in the same cuvette or preparing a new sample for measurement; or whether there are no significant errors such that all measurements are considered acceptable, in which case, all measurements can be used, or more preferably one of the measurements can be used, e.g., the highest or lowest, depending on the type of analysis being conducted.

The present invention thus solves the problems of optically interfering conditions affecting the measurement of a sample through a cuvette by both detecting interfering conditions and determining how the data from all of the measurements should be treated in order to reduce the number of sample re-runs that have to be performed. As used herein an "interfering condition(s)" is anything other than a uniform error in the cuvette (i.e. path-length error) or the sample that will cause an increase or decrease in the emitted light in the measurement area of the cuvette, which condition does not extend across the entire read area of the cuvette. Interfering condition(s) can include permanent interferents such as a spatial defect in the cuvette and fingerprints on the surface of the cuvettes, or transient interferents, such as dirt or dust in the cuvette, dirt or dust on the exterior of the cuvette window, air bubbles in the fluid or sample that was not homogeneously mixed (chemically or thermally).

A significant advantage of the present invention is that precision of analysis can be improved without necessarily eliminating the factors contributing to the imprecision, such as bubbles, etc. Even more significantly, an advantage of the present invention is that a greater number of sample analysis will be useable in spite of the fact that factors leading to outlying reads may be present (i.e., there will be less of a requirement for re-running sample and the time and expense associated therewith). The present invention also allows the user to determine if the uncertainty of the quality of the results is high enough such that the results should be disregarded, thus requiring the user to re-run the analysis using a new sample aliquot.

The method of the present invention can be used in any analysis methodology and analyzer that includes detecting light from a sample to be measured and is broadly referred to herein as spectrophotometry. Some examples include absorption spectrophotometry assays such as end-point reaction analysis and rate of reaction analysis, turbidimetric assays, nephelometric assays, radiative energy attenuation assays (such as those described in U.S. Pat. Nos. 4,496,293 and 4,743,561 and incorporated herein by reference), ion capture assays, colorimetric assays, and fluorometry spectrophotometry assays, and immunoassays, all of which are well known in the art. A preferred analysis technique is absorption spectrophotometry such as end-point reaction analysis and rate of reaction analysis. The preferred embodiments of the present invention are described with reference to absorption spectrophotometry although the broad aspect of the present invention is not so limited.

The sample generally contains an analyte being measured, preferably in a diagnostic assay. Examples include, HDL (high density lipoprotein), which is a generally a two point rate assay. Another example is high sensitivity CRP (C-reactive protein), which is generally a blanked endpoint assay. Still another example is Gentamicin, which can generally be done as an endpoint assay, two point rate assay or multipoint rate assay. However, other analytes can also be measured, such as a chemical analyte in an organic or inorganic medium in an industrial setting, for example, in a quality assurance laboratory or an environmental analysis.

A cuvette is provided for containing the sample. In a preferred embodiment, the cuvette is an open top cuvette adapted for receiving the tip of a pipette or proboscis which dispenses or aspirates sample and/or reagents into the cuvette, such as those described for example in U.S. Patent Application Publication No. 2003/0003591 A1, Des. 290, 170 and U.S. Pat. No. 4,639,135, all of which are incorporated by reference in their entireties. Particularly preferred are cuvettes having a plurality of vertically disposed reaction chambers side-by-side in spaced relation, each of said reaction chambers having an open top and being sized for retaining a volume of sample or reagent as described in the '591 published application.

A source of light and a detector are also provided. The wavelength of light used preferably ranges from mid infrared (approx. 1100 nm) to ultraviolet (approx. 300 nm) depending on the analysis to be performed. The light source can be any well known source such as a photodiode. The detector can be detectors well known for the particular method of analysis. For example, in a spectrophotometric method, the detector can be a photodiode or a charged couple device (CCD), such as a 2 to 5 mega pixel detector.

As noted above, at least two measurements are taken through the sample and cuvette at different spatial locations. The number of measurements can range from 2 up to millions in the case of a mega pixel CCD. The only limitation on the number of measurements is the physical limitation on placing the light source(s) and detector(s) in a proper position with the sample and cuvette to be measured. In a preferred embodiment 3 to 5 measurements are taken through the sample, with 3 measurements being the most preferred, e.g., at locations a, b and c on the cuvette, which preferably correspond to Left(L), Right(R) and Middle(M) positions. It is important that the measurements be taken at different spatial locations to avoid measuring the same interfering condition(s) (e.g. an air bubble) at all the same measurement locations. To achieve measurements at different locations across the cuvette, a single light source is preferably held stationary, while the cuvette is moved relative to the light source. Of course, a single light source may be movable, or multiple stationary lights source may be employed.

As shown in FIG. 1, in a preferred embodiment, multiple measurements are taken spatially across the cuvette (10). As noted above, these spatial measurements are intended to both determine if there is reason to discard the result from this cuvette or to merge the data in a way to produce a more consistent result. In the embodiment shown in FIG. 1, the measurements are spaced 0.024" apart for a total distance of 0.048" (across the three measurements) with a measurement window of 0.059". This enables the detection of interfering condition(s) that are unique to particular areas of the cuvette.

The light beams are transmitted through the cuvette and are partially absorbed depending on the concentration of the analyte in the sample and other factors such as scattering and absorbance due to the interfering condition. The transmitted portion of the beams are measured by the detector which in the case of absorption spectrophotometry is generally located opposite where the beam of light enters the sample and cuvette to result in a sample absorbance A.

An important aspect of the invention is that instead of simply calculating an average sample absorbance based on the multiple measurements, as is done in the known art, the measurements or sample absorbances are compared with one another to determine if at least one of the measurements has been affected by an interfering condition(s) or contaminate. Based on the comparison of sample absorbances, the sample may be handled in the following manner depending on the analysis being carried out: (i) all the sample absorbances may be averaged; (ii) at least one of the sample absorbances may be disregarded and at least one of the other sample absorbances used alone or averaged with another acceptable sample absorbance; and (iii) all the sample absorbances should be disregarded, with the particular sample aliquot of sample being re-measured or discarded and a new sample aliquot being re-run.

In a preferred embodiment, the comparison of sample absorbances is carried out by determining the difference between the compared absorbances. This difference is then compared to a selected absorbance difference. If the absorbance differences between any one of the measurements exceeds the selected absorbance difference, further action is then undertaken as described above and further described below in connection with the preferred embodiments.

In some embodiments, including both endpoint and rate assays described below, a blank measurement A1 may be taken before the sample measurement A2. That is, a blank measurement may be taken before any sample is added to the cuvette, or before reagent is added to the sample already in the cuvette. In the case of slow reactions, it may be possible to measure the blank absorbance after reagents have been added to the sample, but before any significant reaction has taken place. After the blank measurement is obtained, the sample measurement is carried out after adding sample and/or reagent and providing sufficient time for mixing and reaction. The blank absorbance is subtracted from the sample absorbance to yield a corrected absorbance A. The blank measurement will generally contribute to a reduction in some errors, by canceling out errors that are continually present during the analysis, such as marks on the cuvette (e.g., fingerprint smudges) or defects in the cuvette. For example, if a mark on the cuvette in the area of one of the spatial measurements contributes to a 0.03 increase in absorbance, this increase will be present during both the blank and sample measurement. Subtracting the blank absorbance from the sample absorbance will then cancel the 0.03 increase. If no blank measurement is carried out, then the method of the present invention would flag the one measurement as an outlier and take further action as appropriate (e.g., discard the outlier or the entire measurement for that sample). The blank measurement embodiment may be used with the other embodiments of the present invention.

The present invention can be used in both endpoint or rate assays. Both of these assays are well known in the field of spectrophotometry. See, e.g., *Modern Optical Methods of Analysis* by Eugene D Elson 1975, which is incorporated by reference in its entirety. Briefly stated, an endpoint assay takes a single measurement (not including a blank measurement) after reaction between sample and reagents. That is, after development of the chromophore that will absorb the light being transmitted through the sample. Using the present invention with the endpoint assay technique simply requires that the sample measurements, at the different spatial locations on the cuvette, be taken only once, generally after complete development of the chromophore. These measurements are compared with one another according to the present invention.

On the other hand, a rate assay will take at least two measurements for each spatial location at different times after the reagent has been added. Rate assays provide much more data and flexibility. Testing has shown that deliberate interfering condition(s) such as defects or marks made on the surface of the cuvette produce no impact on calculated rate even when these differences are large for the same reason that a blank measurement will result in a reduction of errors. That is, in both assays that include blank measurements and rate assays, a difference in absorbance is being measured, which will cancel out increased absorbance (or decreased absorbance in the case of high absorbances) due to the interfering condition(s), unless the interfering condition obstructs light to the point that the spectrophotometer noise becomes an issue. Based on the different measurements at different times, a rate for each spatial measurement location on the cuvette can be determined. To determine errors, the difference in rates are compared for the various measurement locations.

As noted above, an important feature of the present invention lies in a comparison of the measurements at each different spatial location across the cuvette to determine or detect if an error exists. Based on the comparisons, many different courses of action are available as described in connection with preferred embodiments below.

In one embodiment, each sample absorbance is compared with the other sample absorbance(s). If the difference between any of the absorbances exceeds a selected difference in absorbance, all of the measurements are discarded and the same sample/cuvette is remeasured. Alternatively, a new aliquot of sample or a new cuvette is used and measured. This is less preferred than other embodiments, since it likely entails the necessity of re-running a new sample aliquot at additional time and expense.

The selected difference in absorbance can be pre-determined based on the particular analysis being carried out and the requirements for precision and sensitivity. For example, in an assay that has a calibration curve with a steep slope (i.e., a strong signal to noise ratio), a small variation in absorbance will result in a small change in the predicted concentration of the analyte being assayed. Thus, less precision would be required. In contrast, in an assay that has a calibration curve with a shallow slope (i.e., a weak signal to noise ratio), a small variation in absorbance will result in a significant change in predicted concentration. Thus, more precision will be required and only a relatively small difference in absorbances is generally acceptable.

Alternatively, the selected difference may be determined by the CPU controlling the analyzer during the measurements of the sample(s). Such selection by the CPU may be based on specifications inputted by the operator or software controlling the CPU, and/or trends observed by the CPU during the measurements of multiple samples. For example, the CPU may determine that a greater degree of imprecision will be tolerated for a certain assays, based on previous knowledge of the assay calibration curve slope. That is, as described above, an assay with a large signal (i.e., a steep calibration curve) will tolerate a greater degree of imprecision and thus the selected difference may be greater, while those assays with less signal (i.e., a shallow calibration curve) will require greater precision and thus the selected difference will be less.

If the difference in absorbances is within the selected difference, then all of the absorbance measurements can be averaged and the average absorbance is used in the calculation of the concentration of the substance to be measured in the sample. Alternatively, as described below, one of the absorbances (generally the highest or lowest absorbance) can preferably be selected to determine concentration. In this embodiment, the analysis can be carried out with or without a blank measurement as described above.

In another preferred embodiment, each sample absorbance is again compared with the other sample absorbance(s), preferably all of the other sample absorbances, to determine a difference in absorbances. If the difference between all of the absorbances exceeds a selected difference in absorbance, all of the measurements are discarded and the same sample/cuvette is remeasured. Alternatively, a new aliquot of sample or a new cuvette is measured.

If at least two of the absorbances have differences which are less than the selected difference, these absorbances are used in the calculation of the concentration of the substance being measured. As noted in the embodiment described above, these absorbance measurements can be averaged and the average absorbance is used in the calculation of the concentration of the substance to be measured in the sample. Alternatively, as described below, one of the absorbances (generally the highest or lowest absorbance) can be selected to determine concentration. In this embodiment, the analysis can be carried out with or without a blank measurement as described above.

The selected difference in absorbance can be determined either beforehand or during the analysis by the CPU as described above. This embodiment can be used with or without a blank measurement.

In another preferred embodiment, blank measurements are taken at least two different spatial locations across the cuvette, preferably at the same locations that one or more of the sample measurements will be carried out. The blank absorbances obtained by the blank measurements are then compared with a selected threshold blank absorbance. If the blank absorbance measurements are below the selected threshold blank absorbance value, then one or all of the blank measurements can be used in the further analysis. For example, each blank measurement can be subtracted from its corresponding sample measurement. Alternatively, the lowest blank absorbance or an average blank absorbance can be subtracted from all sample measurements. If one or more blank absorbances, particularly one blank absorbance, are above the threshold absorbance, then this is evidence that a bubble or other interfering condition(s) is present and these blank absorbances should be discarded. The selected threshold absorbance can be predetermined based on previous experience with a particular sample or substance being measured. Alternatively, the selected threshold absorbance can be determined by the analyzer while the samples are being run based on state of the samples, previous analysis of samples, etc.

In a particularly advantageous aspect of the invention, the inventors have discovered that in low absorbance (e.g., an absorbance < one (1) absorbance unit) assay embodiments, the most accurate result generally occurs when the lowest of the at least three sample absorbances (optionally corrected with a blank measurement) for a rate or end point calculation is used. This lowest absorbance measurement is preferably only selected if, for endpoint assays, the three measurements are within an acceptable threshold, or for rate assays, the calculated rate difference from measurement position to measurement position is within an acceptable threshold using the techniques described above. That is, in the same manner above, the at least three sample absorbances are compared to determine if: all the sample absorbances should be disregarded; one or more of the sample absorbances should be disregarded and the remaining absorbances retained; or all the sample absorbances should be averaged. If at least two sample absorbances are retained and an average retained absorbance is less than a selected absorbance then the lowest absorbance is used in determining the presence or concentration of the analyte.

While not being bound by any theory, the inventors believe that the reason for selecting the lowest absorbance measurement for relatively low absorbance assays is that interfering condition(s) have been shown to only increase absorbance. That is, the absorbance caused by the interfering condition(s) relative to the relatively low absorbance of the sample is higher. Thus, the higher absorbance measurements are more likely to be erroneous, since these are more likely due to the interfering condition(s), and the more accurate result will be obtained using the lower absorbance measurements. Conversely, at some threshold of absorbance, which can be determined by those skilled in the art through routine experimentation, interfering condition(s) will tend to decrease the measured absorbance. As a result, at high absorbance measurements, the higher absorbance measurements are more likely to be representative of the true concentration, since the lower absorbance measurements are more likely due to the transient defect. That is, in the same manner above, the at least three sample absorbances are compared. If at least two sample absorbances are retained and an average retained absorbance is greater than or equal to a selected absorbance then the highest absorbance is used in determining the presence or concentration of the analyte.

In a preferred embodiment, the threshold or cutoff absorbance is one (1) absorbance unit (AU). That is for absorbances that are less than one, the lowest absorbance is used in the determination, whereas for absorbances that are greater than or equal to one (1) absorbance unit (AU), the highest absorbance is used in the determination.

As described above, in certain embodiments, if at least two absorbances have a difference in absorbance which is less than a selected difference, then one or an average of the at least two absorbances can be used in the calculation of the concentration of the analyte or substance being measured. In the embodiment described below, the present invention provides a method that can determine which, if any, absorbances can be used if the at least two absorbances have difference which is less than a predetermined limit, which is dependent on the test or assay being performed. The method of this preferred embodiment employs an algorithm that can be used in applications where any one of the three absorbances (in those analysis where three absorbances are employed) is sufficiently different from the other two (i.e., outside the selected difference in absorbance), and which scrutinizes the results if there are two absorbances that agreed (i.e., are within the selected difference in absorbance) to determine if the result is reportable or might be "salvaged," (i.e., the analysis does not have to be re-run).

The algorithm used in the method of this embodiment ("hereinafter referred to as "Algorithm") examines absorbances for certain patterns to determine if the differing or outlying absorbance was really the one affected by a possible interfering condition, such as a bubble or debris in the cuvette cell. If certain pattern conditions are met, a prediction can be made from the two absorbances in agreement. The important condition that is addressed by the Algorithm is one where two absorbances agree, but in fact are both affected by an interfering condition, e.g., bubbles or debris, in a manner that affects both equally (i.e., the disagreeing absorbance or outlier is actually the correct absorbance). The pattern analysis logic of the Algorithm identifies such events. Data suggests that this is a rare event, but one that is important to detect and report as a "no result" should it be encountered, requiring a re-evaluation of the analysis that can include re-running the same sample or analyzing a new aliquot of sample, or some other mode of intervention by the operator.

Figure 2A:
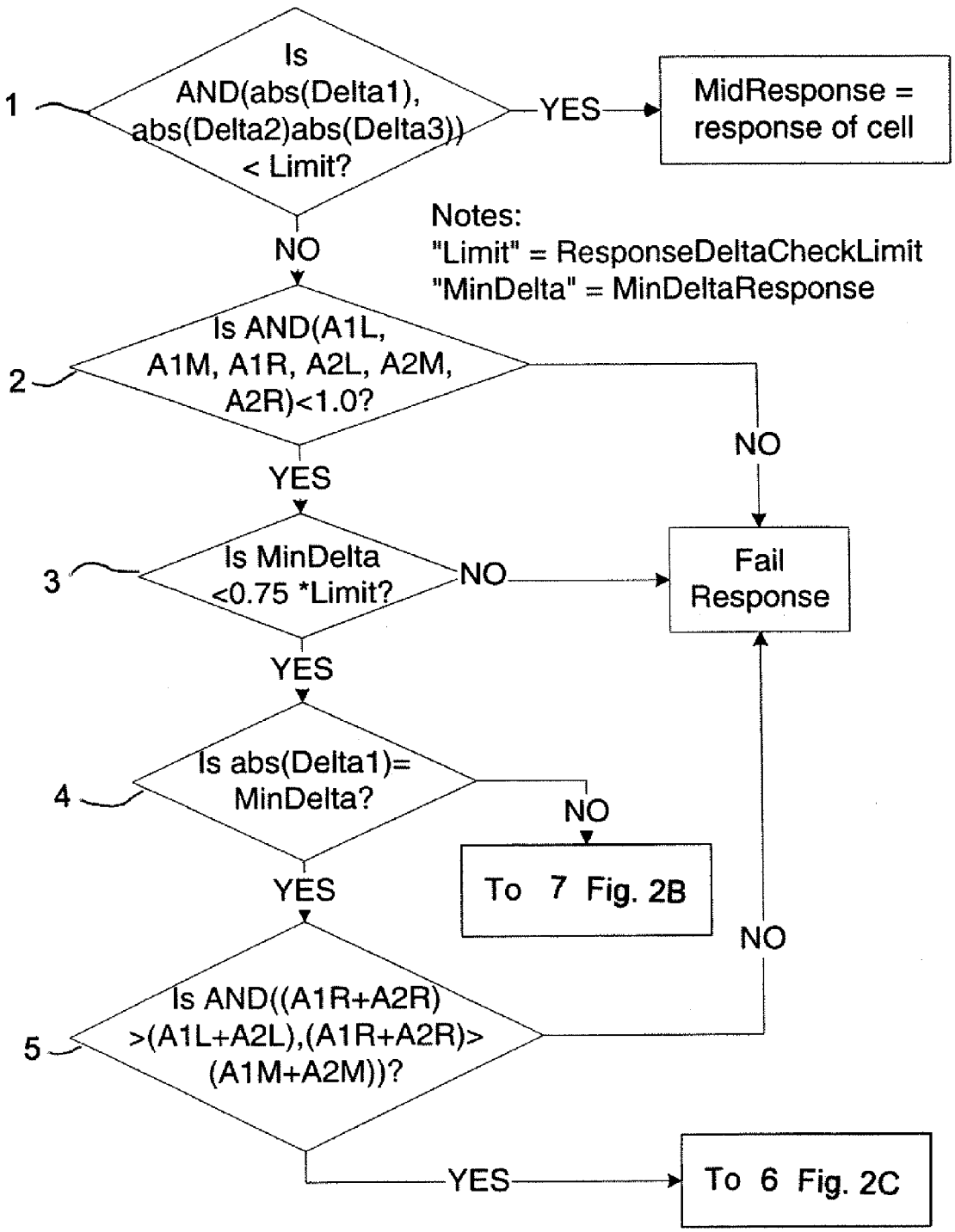
FIGS. 2A-C are a flow diagram showing the logic of an algorithm for determining whether one or more absorbances should be retained or the analysis re-evaluated according to a preferred embodiment of the present invention.
Figure 2B:
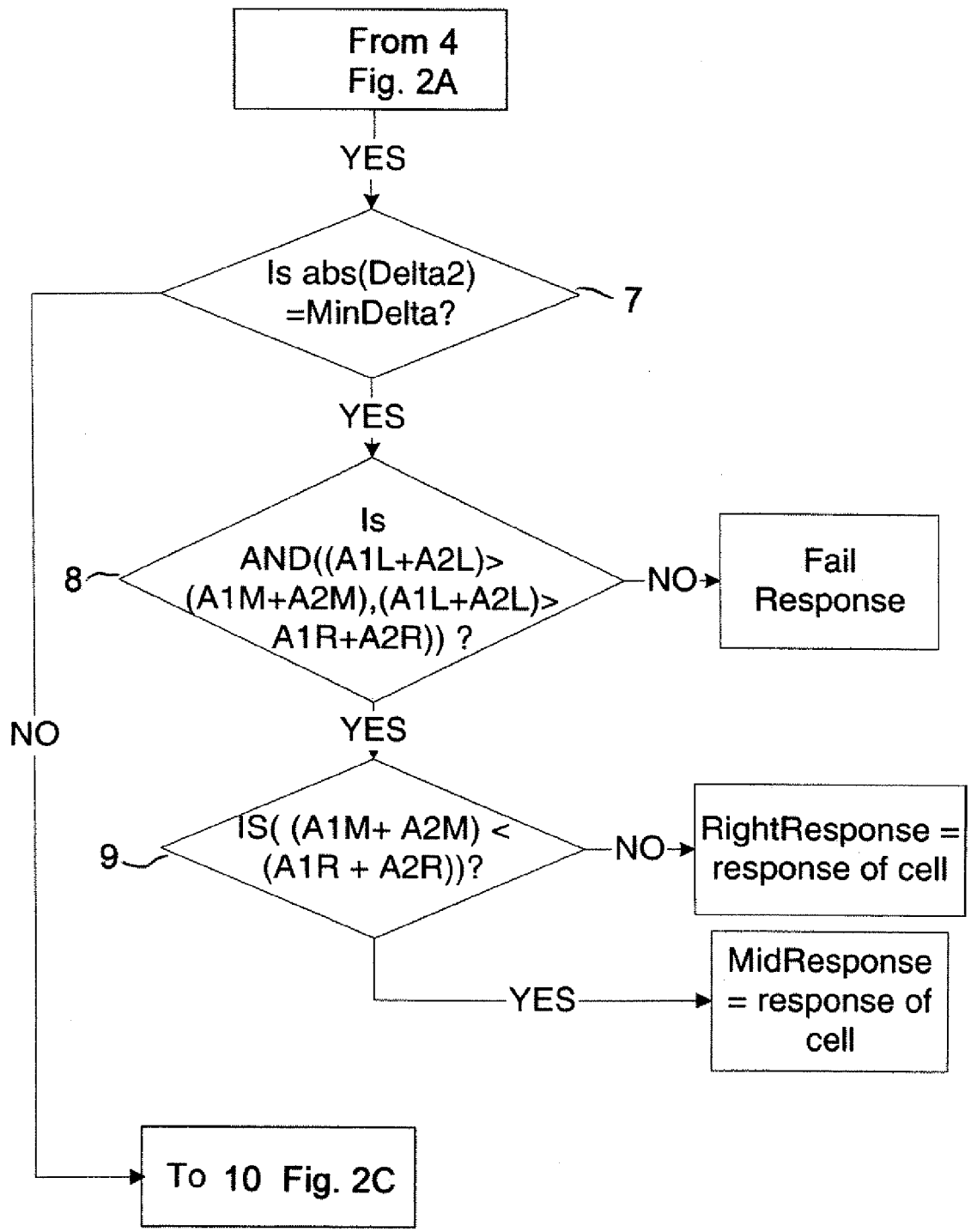
Figure 2C:
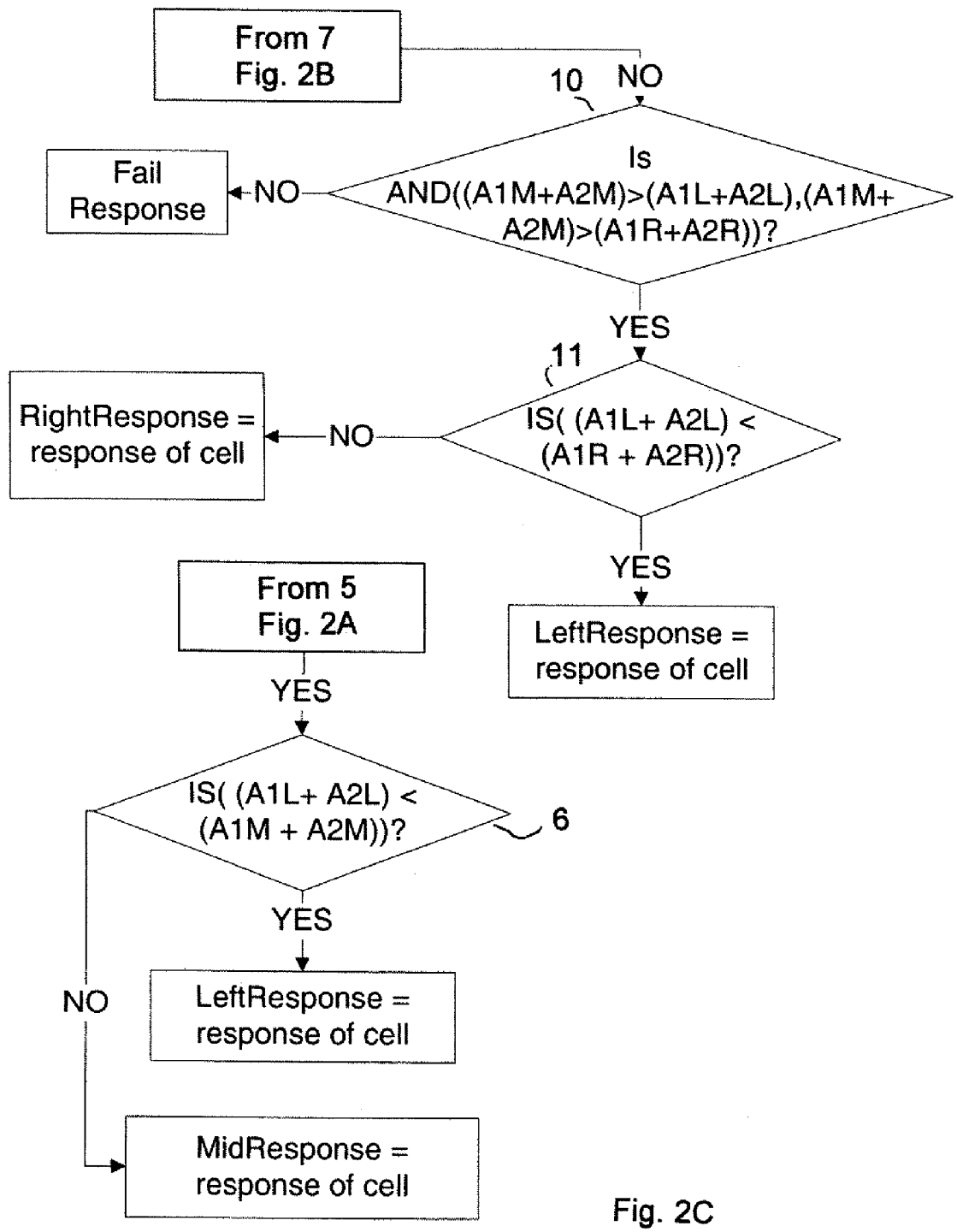

FIGS. 2A-C are a block diagram detailing the logic of the Algorithm. Definitions are provided as follows (in the Figures and below, "read" and "absorbance" are used interchangeably):

Axy=Read identifier, x=1 (first read, e.g., blank), 2 (second read); y=a, b, c (read position, preferably L, M, R, left, middle, or right). Example: "A1M"=Read 1, middle position. "A2c"=Read 2, position c.

Left Response (Resp 1)=A2L−A1L. If the math model is a rate assay, then Left Response (Resp 1)=(A2L−A1L)/(Read 2 time−Read 1 time).

MidResponse (Resp 2)=A2M−A1M. If the math model is a rate assay, then MidResponse (Resp 2)=(A2M−A1M)/(Read 2 time−Read 1 time).

RightResponse (Resp 3)=A2R−A1R. If the math model is a rate assay, then RightResponse (Resp 3)=(A2R−A1R)/(Read 2 time−Read 1 time).

Limit (corresponds to the predetermined limit described above)=intercept+slope * (minimum of Resp1, Resp2, or Resp3); note that intercept and slope are assay specific.

Delta1=Resp1−Resp2. Alternatively, "Delta" can be described as the difference between each pair of absorbances.

Delta2=Resp2−Resp3.

Delta3=Resp3−Resp1.

Min Delta=min(abs(Delta1), abs(Delta2),abs(Delta3)). Alternatively, the absolute minimum of Delta can be represented by e.g., |Delta1| or |(A2L−A1L)−(A2M−A1M)| using standard mathematical symbols.

Max Delta=max(abs(Delta1), abs(Delta2),abs(Delta3))

Fail Response=a condition where the three absorbances do not meet acceptance checks of the Algorithm. In this event, "no result" is reported for the test rather than a concentration prediction and the analysis must be re-evaluated.

The reference numerals in the FIGS. 2A-C Algorithm Flow Chart (e.g., 1) correspond to the following description in points 1 through 11 below. Although the description below is with reference to left, right and middle positions (L, R, M), the present invention is not so limited. For example, the position could be top, center and bottom. Thus, an alternative designation of description can be location a, b and c as described above.

1. The first Decision Block indicated by 1 is a check to see if Delta1, Delta 2, and Delta3 are all less than the Limit. If so, the result is predicted from the center absorbance in a preferred embodiment. If this condition is not satisfied, the Algorithm moves to decision point 2 for further evaluation of the data (and possibly "salvaging" the result). Prior to the present invention, the analyzer would have simply failed the response and issued a "no result" resulting in the necessity to re-evaluate.

2. Decision Block 2 checks to see if all optical absorbances are less than 1.0 AU (optical absorbance units) for this particular embodiment. As noted above, in the lower range of AU levels (1.0 is a conservative cutoff), bubbles and particulates in the optical pathway of the cuvette tend to raise the AU level of the absorbance by scattering, back reflecting, or diffracting the incident light. This is an important check as a precursor to the data pattern checks that are described in this embodiment. If all absorbances do fall below 1.0 AU, then the evaluation process continues. If not, then the response is failed and a "no result" issued.

3. Decision Block 3 is a check to see whether or not the two absorbances that agree actually agree exceptionally well (within 75% of the Limit according to this embodiment). If so, then the then the evaluation process continues. If not, then the response is failed and a "no result" issued.

4. Decision Block 4 is the first of several checks to determine which pair of the three absorbances is the one having the exceptional agreement. If Delta1 corresponds to the MinDelta (i.e., the smallest absolute value of the difference between each pair of absorbances), then patterns checks are initiated to determine if either LeftResponse or MidResponse might be used for a prediction. If Delta1 does not correspond to MinDelta, then decision block 7 performs a similar check on Delta2.

Figure 3:
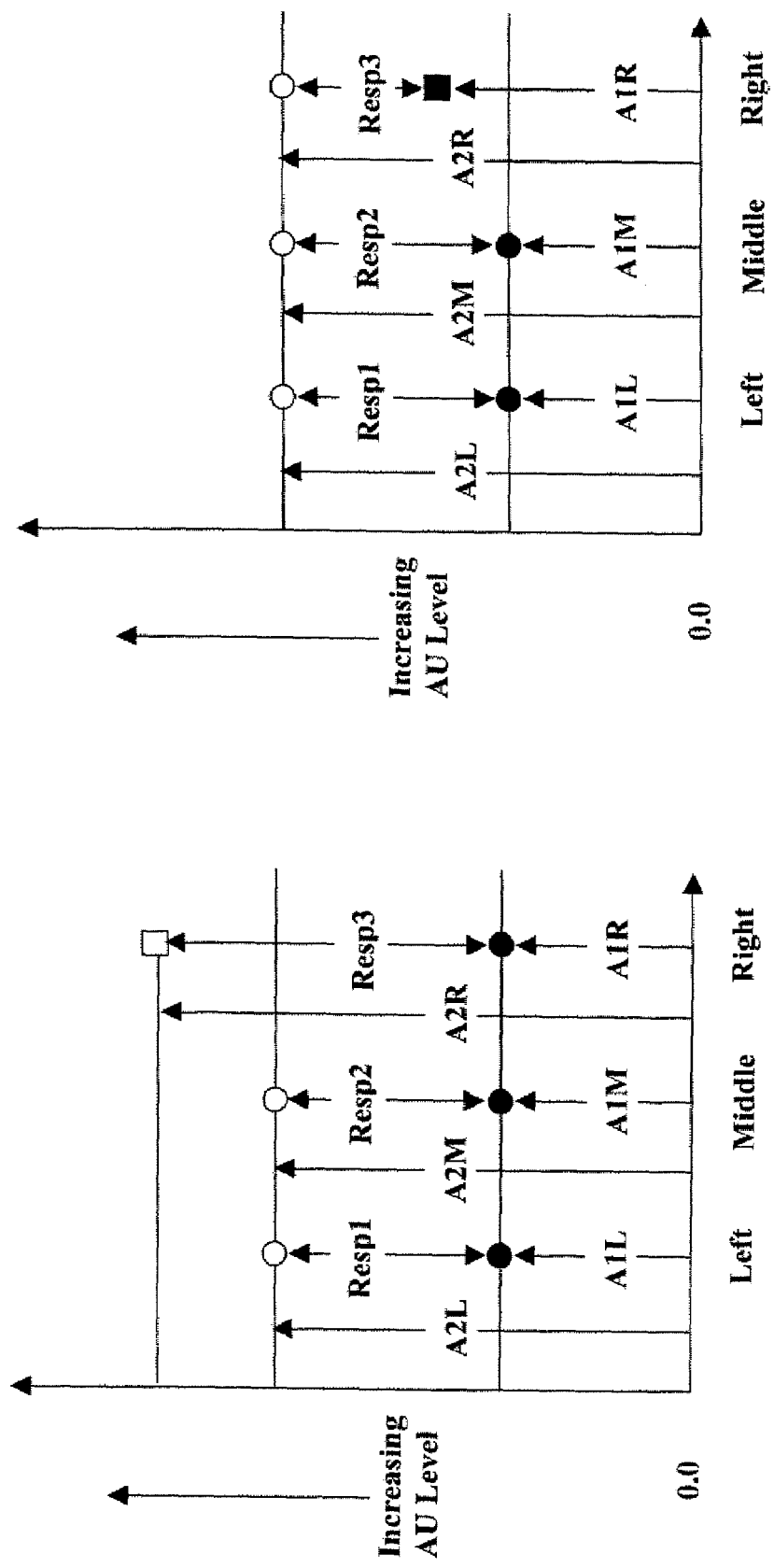
FIG. 3 is a graphical representation of patterns of absorbances or reads that would pass the criteria of Decision Block 5 of FIGS. 2A-C.
Figure 4:
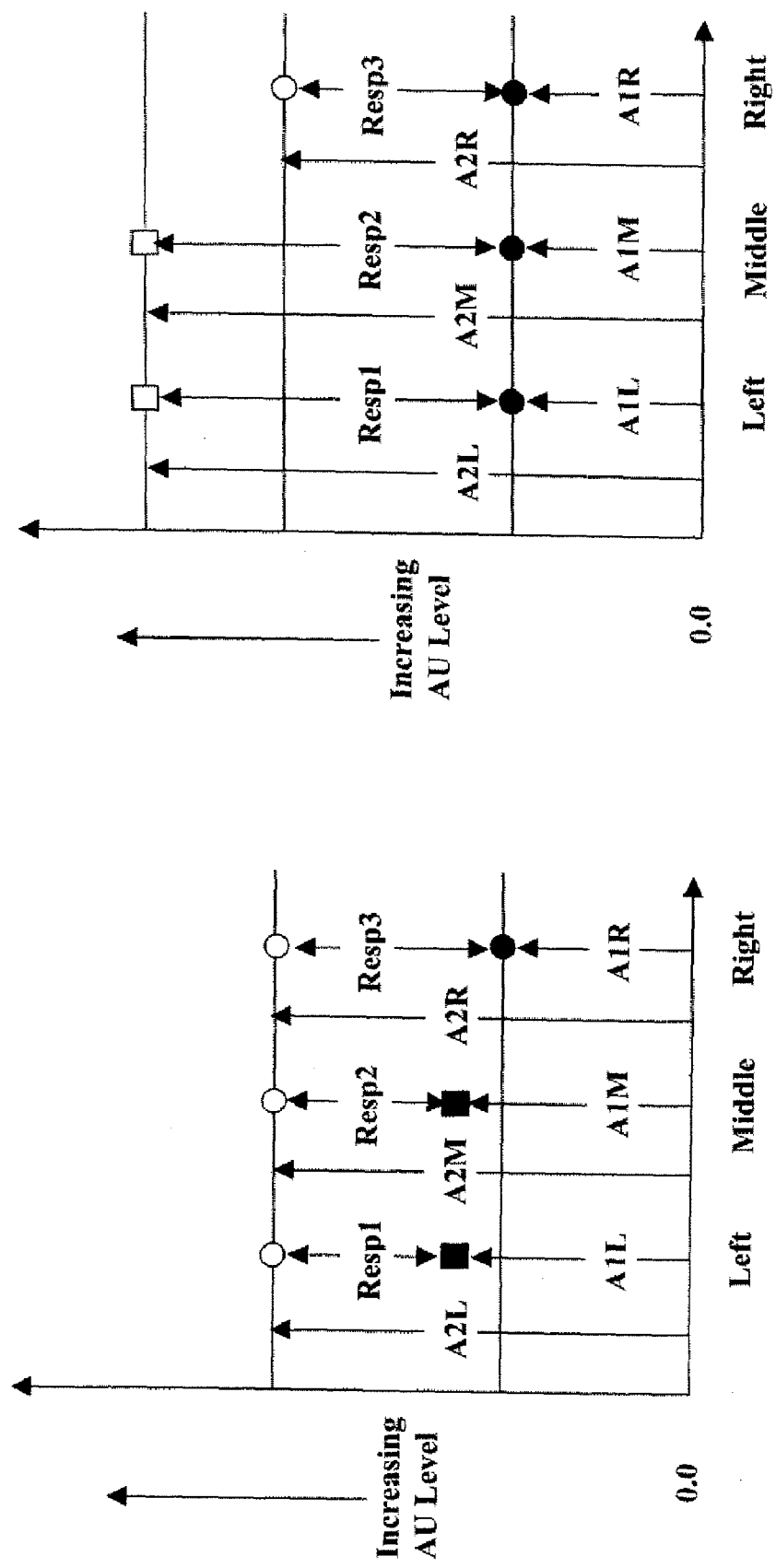
FIG. 4 is a graphical representation of patterns of absorbances or reads that would fail the criteria of Decision Block 5 of FIGS. 2A-C.

5. Decision Block 5 is a pattern check performed to determine if either LeftResponse or MidResponse might be used for a prediction. The mathematics in this block determine if the sum of the right absorbances are a.) greater than the sum of the middle absorbances and are b.) greater than the sum of the left absorbances. If this assessment is true, then a prediction of the correct pair using either the left or middle absorbances will be performed (Decision Block 6). FIG. 3 shows examples of patterns that would pass the Decision Block 5 criteria (concludes that A1R and/or A2R is elevated and may have been affected by an interfering conditions such as a bubble or debris in the cuvette). In FIGS. 3-8, the solid circles and squares represent the first absorbances and the outlined circles and squares represent the second absorbances. The circles are absorbances unaffected by interfering conditions, e.g., bubbles, debris, and the squares represent absorbances affected by interfering conditions. FIG. 4 shows examples of patterns that would fail the Decision Block 5 criteria (concludes that the left and middle absorbances are actually the absorbances that have been affected by bubbles or debris in the cuvette and happen to agree with one another by chance). A failure in this Decision Block results in a "failed response" (i.e., no result).

6. Decision Block 6 performs the final selection of the absorbance set (either left or middle in this embodiment) to serve as the response pair and ultimately make a result prediction with. The Decision Block selects the pair of absorbances having the lowest numerical sum, the idea being that this is the "cleanest" absorbance set (i.e., interfering conditions such as bubbles and debris only act to raise AU levels in the ranges described in this embodiment).

7. Decision Block 7 is analogous to Decision Block 4. It checks to see if Delta2 is the MinDelta. If so, then pattern tests are performed in Decision Block 8 that examines the nature of the left absorbance (since the middle and right absorbances agree the best). If not, then the algorithm moves to Decision Block 10 that examines the nature of the middle absorbance (since the left and right absorbances agree the best).

Figure 5:
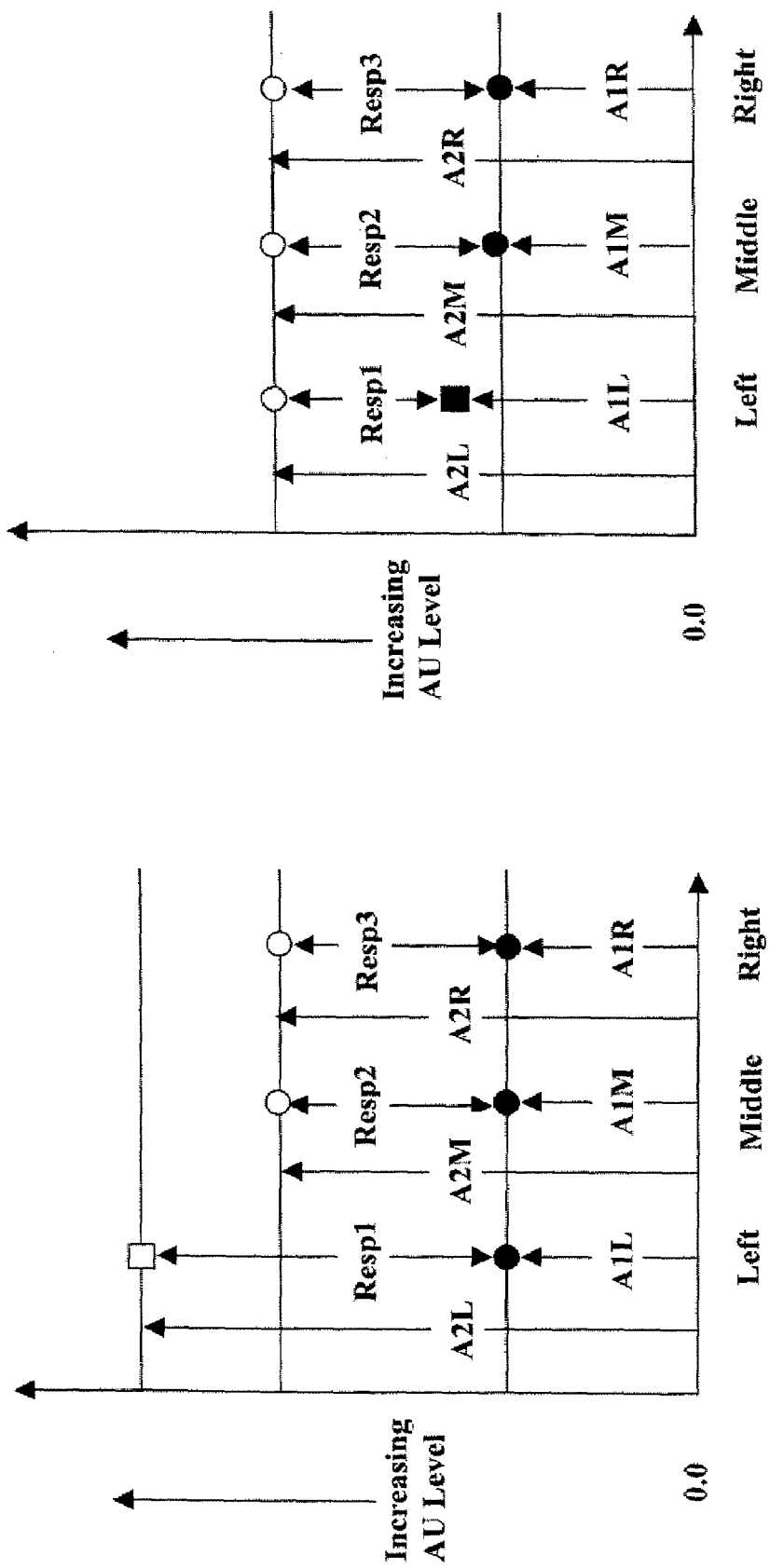
FIG. 5 is a graphical representation of patterns of absorbances or reads that would pass the criteria of Decision Block 8 of FIGS. 2A-C.
Figure 6:
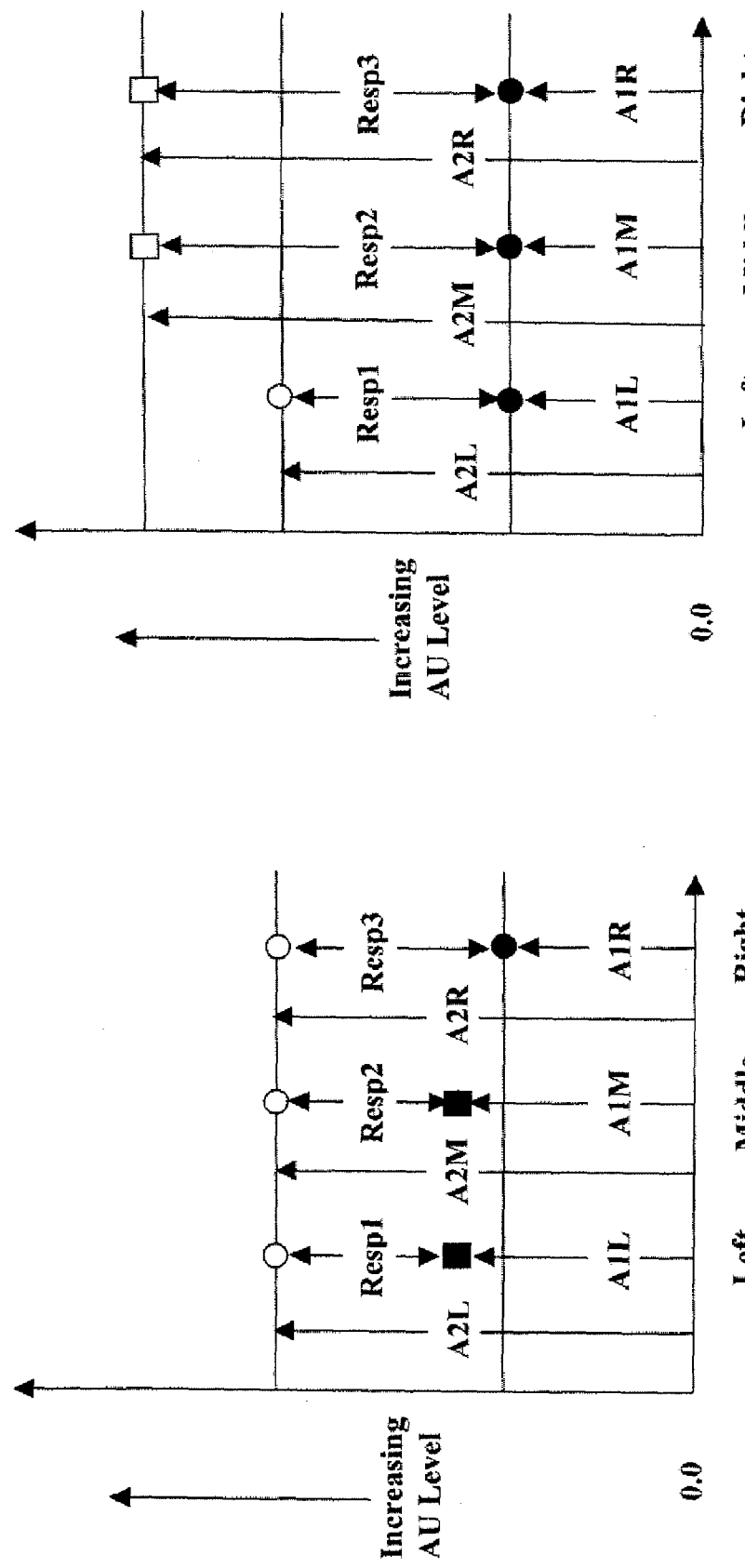
FIG. 6 is a graphical representation of patterns of absorbances or reads that would fail the criteria of Decision Block 8 of FIGS. 2A-C.

8. Decision Block 8 is analogous to Decision Block 5. It is a pattern check performed to determine if either MidResponse or RightResponse might be used for a prediction. The mathematics in this block determine if the sum of the left absorbances are a.) greater than the sum of the middle absorbances and are b.) greater than the sum of the right absorbances. If this assessment is true, then a prediction using either the middle or right absorbances will be performed (Decision Block 9). FIG. 5 shows examples of patterns that would pass the Decision Block 8 criteria (concludes that A1L and/or A2L is elevated and may have been affected by a bubble or debris in the cuvette. FIG. 6 shows examples of patterns that would fail the Decision Block 8 criteria (concludes that the middle and right absorbances are actually the absorbances that have been affected by bubbles or debris in the cuvette and happen to agree with one another by chance). A failure in this Decision Block results in a "failed response" (i.e., no result).

9. Decision Block 9 is analogous to Decision Block 6. It performs the final selection of the absorbance set (either middle or right) to serve as the response pair and ultimate make a result prediction with. The Decision Block selects the pair of absorbances having the lowest numerical sum, the idea being that this is the "cleanest" absorbance set (i.e., bubbles and debris only act to raise AU levels in the ranges of the present embodiment).

Figure 7:
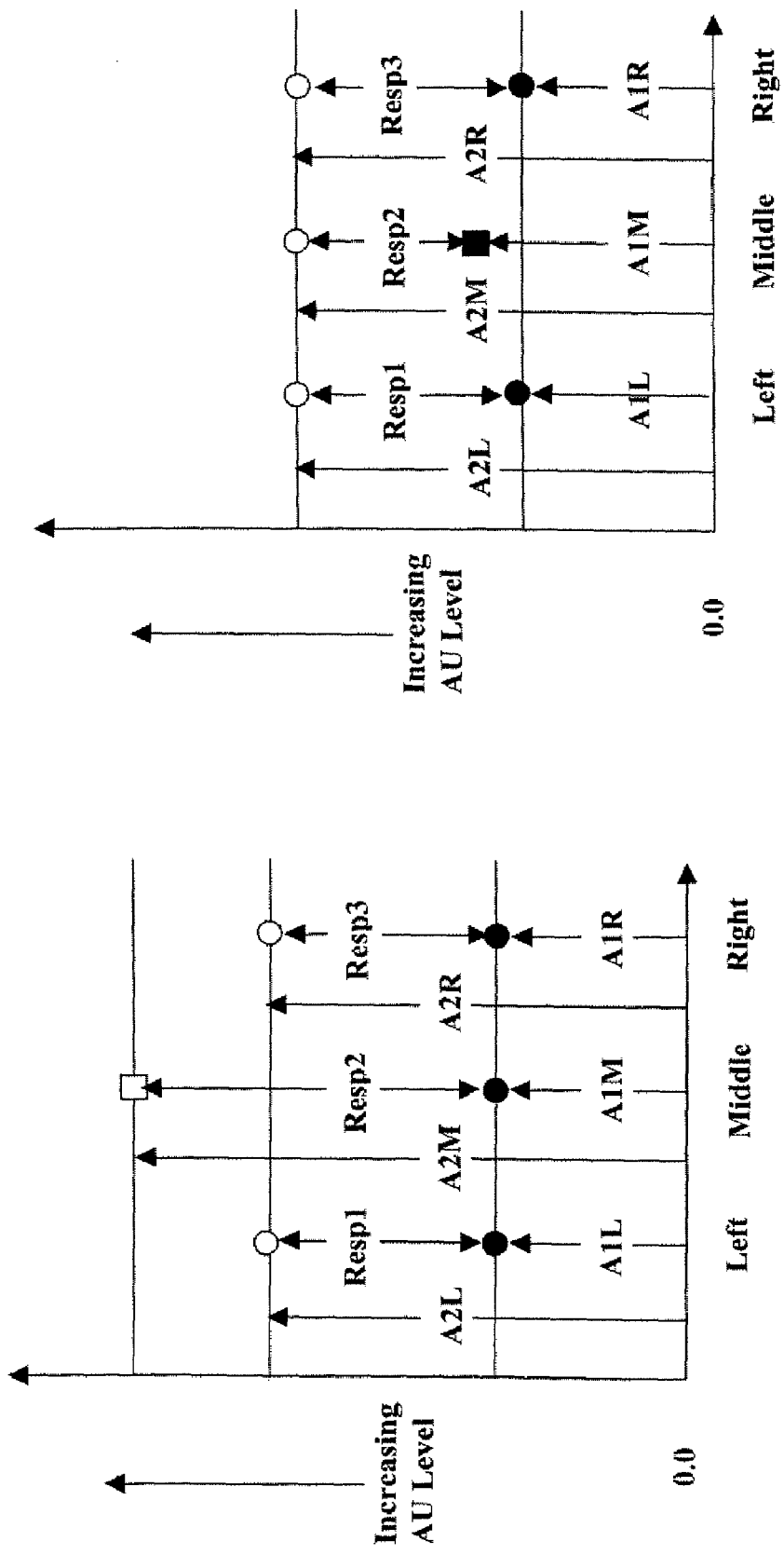
FIG. 7 is a graphical representation of patterns of absorbances or reads that would pass the criteria of Decision Block 10 of FIGS. 2A-C.
Figure 8:
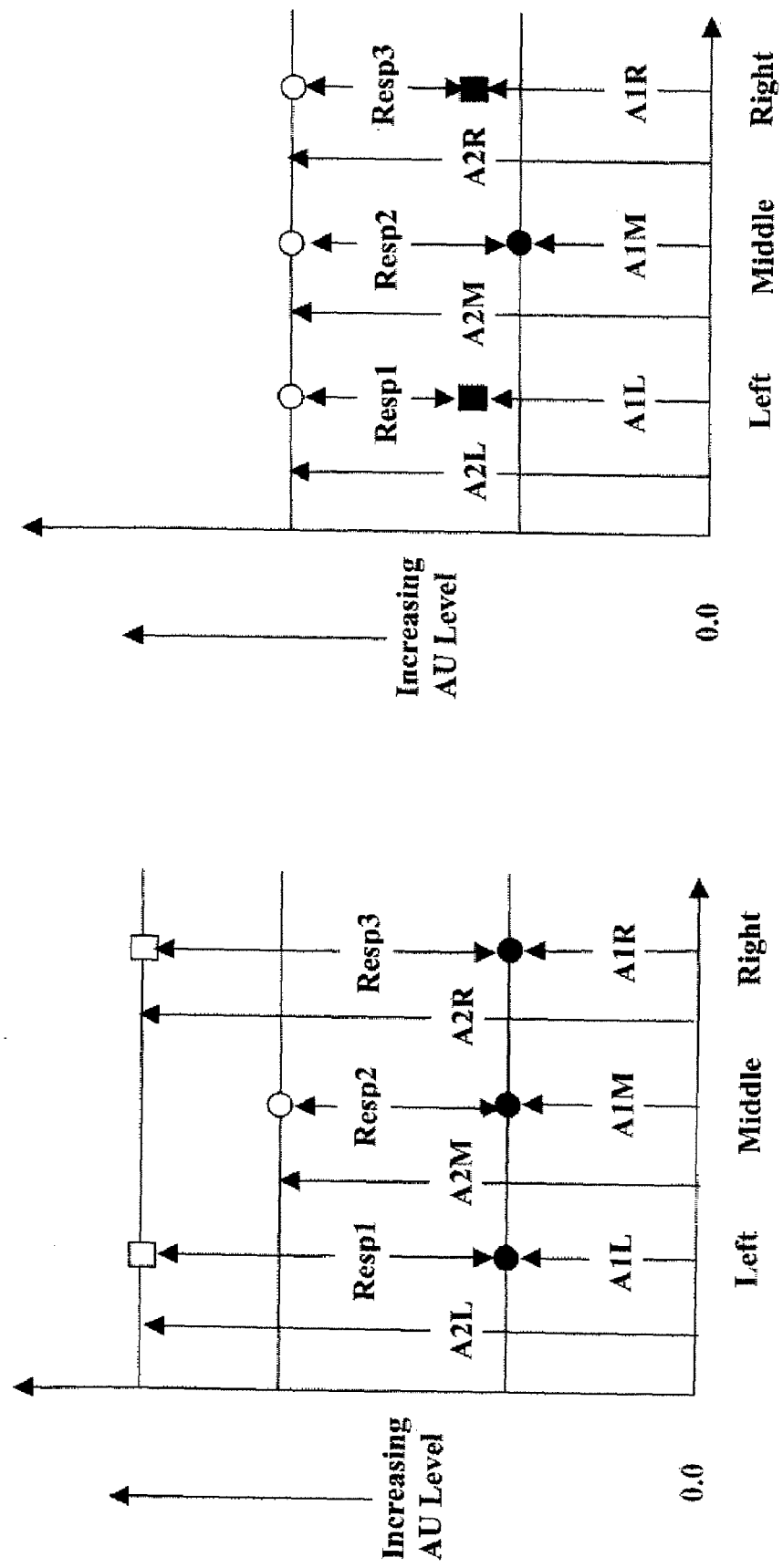
FIG. 8 is a graphical representation of patterns of absorbances or reads that would fail the criteria of Decision Block 10 of FIGS. 2A-C.

10. Decision Block 10 is analogous to Decision Blocks 5 and 8. It is a pattern check performed to determine if either LeftResponse or RightResponse can be used for a prediction. The mathematics in this block determine if the sum of the middle absorbances are a.) greater than the sum of the left absorbances and are b.) greater than the sum of the right absorbances. If this assessment is true, then a prediction using either the left or right absorbances will be performed (Decision Block 11). FIG. 7 shows examples of patterns that would pass the Decision Block 10 criteria (concludes that A1M and/or A2M is elevated and may have been affected by a bubble or debris in the cuvette. FIG. 8 shows examples of patterns that would fail the Decision Block 10 criteria (concludes that the left and right absorbances are actually the absorbances that have been affect by bubbles or debris in the cuvette and happen to agree with one another by chance). A failure in this Decision Block results in a "failed response" (i.e., no result) and the analysis will have to be re-evaluated.

11. Decision Block 11 is analogous to Decision Block 6 and 9. It performs the final selection of the absorbance set (either left or right) to serve as the response pair and ultimate make a result prediction with. The Decision Block selects the pair of absorbances having the lowest numerical sum, the idea being that this is the "cleanest" absorbance set (i.e., bubbles and debris only act to raise AU levels in the ranges of the present embodiment).

The Algorithm according to this preferred embodiment can reduce the number of tests flagged for a multiple, e.g., triple absorbance failure (no results) by as much as 50% over previous algorithms, such as (if DeltaX (X=1, 2, 3)>Limit, then no result). In experiments done by the inventors there are no analysis where a result was saved that should have been rejected.

EXAMPLE

Figure 9:
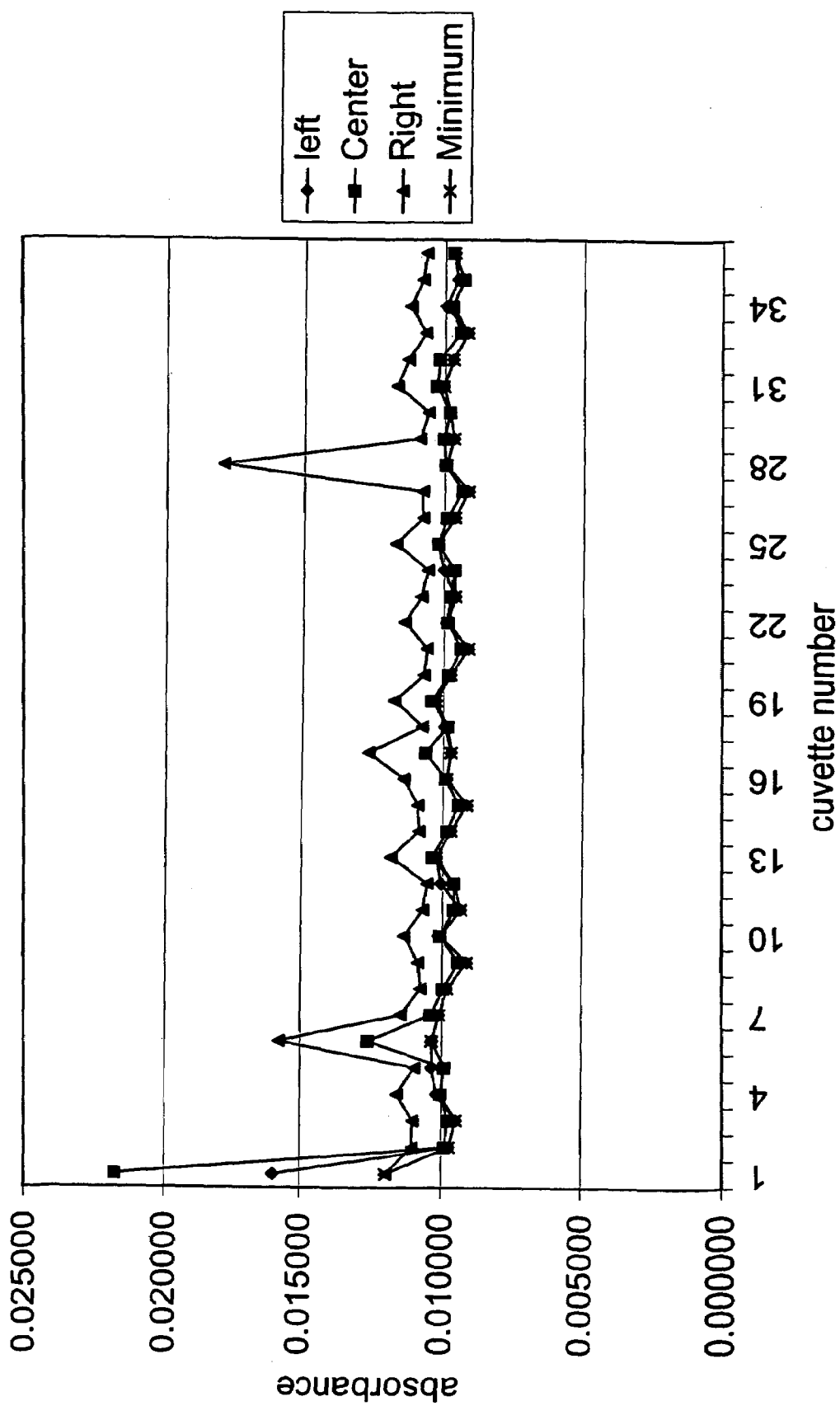
FIG. 9 is a graph showing the measurement of the concentration of C-reactive protein in 36 cuvettes with 3 measurements for each cuvette.

An assay for C-reactive protein (CRP) having a known concentration of 0.582 mg/dl was prepared and analyzed in 36 different cuvettes. For each cuvette an absorbance measurement was taken in the left, center and right of the cuvette. The results for each measurement in each cuvette is plotted in FIG. 9 with lines marked with diamonds (◊) for the left, squares (■) for the center and triangles (▲) for the right. As FIG. 9 shows, there were significant outliers for cuvettes Nos. 1, 6 and 28 as shown on the x-axis. These were likely due to the presence of air bubbles in the cuvettes. Even though there were significant outliers in these cuvettes, only the results in cuvette 1 would be rejected in a clinical setting, since a comparison between the absorbances would yield a difference that was outside an acceptable threshold. In the remaining results with outliers, while the differences in absorbance between the right and other reads were significant, the difference in absorbance between the center and left read was within acceptable threshold. Thus, these results can be used in a clinical setting without the need to re-run the samples again. In addition, to improve the accuracy of the results, the lowest absorbance measurement can be used to determine the concentration of CRP, because of the low absorbance (<1) measurements for these samples. The higher absorbance readings (even those within an acceptable threshold of absorbance difference) were likely due to the presence of interfering conditions.

FIG. 10 illustrates the example of FIG. 9 slightly differently. Specifically, FIG. 10 shows the standard deviation (SD) for different locations on the cell and for the minimum absorbance on each cell, regardless of read location. The line marked with diamonds (◊) was the standard deviation when all of the cells were included, including the significant outliers for cuvettes Nos. 1, 6 and 28 as shown in FIG. 9. As shown in FIG. 10, the standard deviation for all locations (left, center and right) and the minimum (for each cuvette) was greatest when the absorbance for all cuvettes were included. The line marked with triangles (▲) was the standard deviation when only cuvette 1 was excluded from the standard deviation calculation. As shown in FIG. 10, the standard deviation for all locations and the minimum was less than the standard deviation that included all cuvettes. The line marked with squares (■) was the standard deviation when cuvettes 1, 6 and 28 were excluded. As shown in FIG. 10, the standard deviation for all locations and the minimum was the least when cuvettes 1, 6 and 28 were excluded.

The measurement method according to the present invention can be implemented by a computer program, having computer readable program code, interfacing with the computer controller of the analyzer as is known in the art.

It will be apparent to those skilled in the art that various modifications and variations can be made to the compounds, compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

We claim:

1. An article of manufacture comprising a computer usable medium having computer readable code configured to conduct a method for measuring the presence or concentration of an analyte in a sample by spectrophotometry, comprising:
    providing an open top cuvette having a sample with an analyte to be measured;
    providing a light source and a detector for detecting emitted light;
    taking at least two measurements that includes:
        (i) directing at least two beams of light from the light source to different locations on the cuvette;
        (ii) passing the at least two beams through the cuvette at their respective locations and through the sample to be measured; and
        (iii) measuring at least two respective emitted light beams with the detector; and
    comparing the at least two emitted light beams to determine if: all the emitted light beams should be disregarded; one or more of the emitted light beams should be disregarded; or the emitted light beams should be averaged.

2. An article of manufacture as claimed in claim 1, further comprising taking at least three measurements and comparing the at least three emitted light beams to determine if: all the emitted light beams should be disregarded; one or more of the emitted light beams should be disregarded; or the emitted light beams should be averaged.

3. An article of manufacture as claimed in claim 1, wherein the spectrophotometry is fluorescence spectrophotometry.

4. An article of manufacture as claimed in claim 1, wherein the spectrophotometry is absorption spectrophotometry and the step of taking at least two measurements includes:
    (i) directing at least two beams from the light source to different locations on the cuvette;
    (ii) passing the at least two beams through the cuvette at their respective locations and through the sample to be measured; and
    (iii) measuring at least two respective sample absorbances from the emitted light corresponding to the at least two beams with the detector; and
    comparing the at least two sample absorbances to determine if: all the sample absorbances should be disregarded; one or more of the sample absorbances should be disregarded; or the sample absorbances should be averaged.

5. An article of manufacture as claimed in claim 1, wherein a single light source and a single detector are provided and the cuvette is moved relative to the light source and cuvette to produce the at least two beams of light.

6. An article of manufacture as claimed in claim 4, wherein prior to the step of directing at least two beams, the method further comprises:
    (i) directing at least two beams of light from the light source at their respective different locations on the cuvette;
    (ii) passing the at least two beams through the cuvette alone or the cuvette and sample before the sample has reacted with reagents; and
    (iii) measuring at least two respective blank absorbances from the emitted light corresponding to the at least two beams with the detector; and
    selecting at least one blank absorbance; and
    subtracting at least one blank absorbance from the at least two sample absorbances to result in corrected sample absorbances.

7. An article of manufacture as claimed in claim 6, wherein a single light source and a single detector are provided and the cuvette is moved relative to the light source and cuvette to produce the at least two beams of light.

8. An article of manufacture as claimed in claim 6, wherein all blank absorbances are selected and each blank absorbance is subtracted from its corresponding sample absorbance at the same location.

9. An article of manufacture as claimed in claim 6, wherein the lowest blank absorbance is selected and the lowest blank absorbance is subtracted from each sample absorbance.

10. An article of manufacture as claimed in claim 4, wherein after a period of time after the at least two measurements, the method further comprises:
    taking at least two second measurements at the same location as the at least two measurements to result in at least two second sample absorbances;
    subtracting the at least two sample absorbances from the second sample absorbances to result in a rate sample absorbance.

11. An article of manufacture as claimed in claim 4, wherein the comparison includes comparing the sample absorbances with each other, and if a difference in absorbance between any two absorbances exceeds a predetermined absorbance, then disregarding all sample absorbances.

12. An article of manufacture as claimed in claim 4, wherein the comparison includes comparing the sample absorbances with each other:
    if a difference in absorbance between all absorbances exceeds a predetermined absorbance, then disregarding all sample absorbances;
    if the difference between a predetermined number of absorbances, which is less than the total number of absorbances, is within the predetermined absorbance, then discarding the remaining absorbances and averaging the absorbances of the predetermined number of absorbances.

13. An article of manufacture as claimed in claim 6, wherein the comparison includes comparing the corrected sample absorbances with each other:
- if a difference in absorbance between all absorbances exceeds a predetermined absorbance, then disregarding all sample absorbances;
- if the difference between a predetermined number of absorbances, which is less than the total number of absorbances, is within the predetermined absorbance, then discarding the remaining absorbances and averaging the absorbances of the predetermined number of absorbances.

14. An article of manufacture as claimed in claim 6, wherein the comparison includes comparing the corrected sample absorbances with each other, and if a difference in absorbance between any two corrected sample absorbances exceeds a predetermined absorbance, then disregarding all corrected sample absorbances.

15. An article of manufacture as claimed in claim 1, wherein the comparison detects errors caused by one or more interfering condition(s).

16. An article of manufacture as claimed in claim 15, wherein the interfering condition(s) include air bubbles, finger prints, dirt or defects in the cuvette.

17. An article of manufacture as claimed in claim 2, wherein the analysis is performed on a diagnostic analyzer.

18. An article of manufacture as claimed in claim 1, wherein the light has a wavelength in the range of 300 to 1100 nm.

19. An article of manufacture comprising a computer usable medium having computer readable code configured to conduct a method for measuring the presence or concentration of an analyte in a sample by absorption spectrophotometry, comprising:
- providing a cuvette having a sample with an analyte to be measured;
- providing a source of light and a detector for detecting the light;
- taking at least three measurements that includes:
  - (i) directing at least three beams of the light to different locations on the cuvette;
  - (ii) passing the at least three beams through the cuvette at their respective locations and through the sample to be measured; and
  - (iii) measuring at least three respective sample absorbances of the transmitted beams with the detector; and
- comparing the at least three sample absorbances to determine if: all the sample absorbances should be disregarded; one or more of the sample absorbances should be disregarded and the remaining absorbances retained; or all the sample absorbances should be averaged,
- wherein: if at least two sample absorbances are retained and an average retained absorbance is less than a first selected absorbance then the lowest absorbance is used in determining the presence or concentration of the analyte; or if at least two sample absorbances are retained and an average retained absorbance is greater than or equal to a second selected absorbance then the highest absorbance is used in determining the presence or concentration of the analyte.

20. An article of manufacture as claimed in claim 19, wherein a single light source and a single detector are provided and the cuvette is moved relative to the light source and cuvette to produce the at least three beams of light.

21. An article of manufacture as claimed in claim 19, wherein the first and second selected absorbances are both one absorbance unit.

22. An article of manufacture as claimed in claim 19, wherein the average retained absorbance is based on all sample absorbances.

23. An article of manufacture as claimed in claim 19, wherein prior to the step of directing at least three beams, the method further comprises:
- (i) directing at least three beams of the light at their respective different locations on the cuvette;
- (ii) passing the at least three beams through the cuvette alone or the cuvette and sample before the sample has reacted with reagents; and
- (iii) measuring at least three respective blank absorbances of the transmitted beams with the detector; and
- selecting at least one blank absorbance; and
- subtracting at least one blank absorbance from the at least three sample absorbances to result in corrected sample absorbances.

24. An article of manufacture comprising a computer usable medium having computer readable code configured to conduct a method for measuring the presence or concentration of an analyte in a sample by absorption spectrophotometry, comprising:
- (A) providing a cuvette having a sample with an analyte to be measured;
- (B) providing a source of light and a detector for detecting the light;
- (C) taking at least three measurements that includes:
  - (i) directing at least three beams of the light to different locations a, b and c on the cuvette;
  - (ii) passing the at least three beams through the cuvette at their respective locations a, b and c and through the sample to be measured; and
  - (iii) measuring at least three respective sample absorbances Aa, Ab and Ac of the transmitted beams with the detector;
- (D) determining the absolute value of the difference between each pair of absorbances to arrive at |Aa−Ab|, |Ac−Ab| and |Ac−Aa|;
- (E) comparing an absolute value of the difference between each pair of absorbances with a predetermined limit;,
- (F) if one or more of each the absolute value of the difference is ≧ the predetermined limit, then compare each absorbance to a predetermined absorbance:
  - (i) if one or more absorbances are above the predetermined absorbance, then disregard all readings and proceed to step (K); or
  - (ii) if all absorbances are below the predetermined absorbance, then
- (G) determine the smallest absolute value of the difference between each pair of absorbances;
- (H) determine if the smallest absolute value of the difference is <a predetermined fraction of the predetermined limit:
  - (i) if the smallest absolute value of the difference is not less than the predetermined fraction of the limit then disregard all readings and proceed to step (K); or
  - (ii) if the smallest absolute value of the difference is less than the predetermined fraction of the limit, then
- (I) determine which of the absolute value of the difference between each pair of absorbances is the smallest absolute value of difference;
- (J) determine which absorbance in the smallest absolute value should be selected or if the results should be disregarded; and (K) either re-evaluating the analysis if the results should be disregarded in steps (F), (H) or (J), or calculating the presence concentration of the analyte in the sample by using the selected absorbance.

25. An article of manufacture according to claim 24, wherein prior to the step of directing at least three beams, the method further comprises:
 (i) directing at least three beams of the light at their respective different locations a, b and c on the cuvette;
 (ii) passing the at least three beams through the cuvette alone or the cuvette and sample before the sample has reacted with reagents;
 (iii) measuring at least three respective blank absorbances $A1a$, $A1b$ and $A1c$ of the transmitted beams with the detector;
 (iv) determining the sample absorbance Aa, Ab, and Ac by subtracting the blank absorbance $A1a$, $A1b$ and $A1c$ from measured sample absorbance $A2a$, $A2b$ and $A2c$ respectively;
 wherein the step (J) of determining which absorbance in the smallest absolute value of the difference between each pair of absorbances should be selected or if the results should be disregarded comprises:
 (J1) if the smallest absolute value of the difference between each pair of absorbances is $|(A2a-A1a)(A2b-A1b)|$, then if $A1c+A2c$ is greater than each of $A1a+A2a$ and $A1b+A2b$, compare $A1a+A2a$ and $A1b+A2b$, if $A1a+A2a \leqq A1b\ A2b$ then absorbance Aa is the selected absorbance, otherwise absorbance Ab is the selected absorbance, if $A1c\ A2c <$ is to one of $A1a+A2a$ and $A1b+A2b$, then disregard all readings and proceed to step (K);
 (J2) if the smallest absolute value of the difference between each pair of absorbances is $|(A2c-A1c)-(A2b-A2b)|$, then if $A1a+A2a$ is greater than each of $A1b\ A2b$ and $A1c+A2c$, compare $A1c+A2c$ and $A1b\ A2b$, if $A1c+A2c < A1b+A2b$ then absorbance Ac is the selected absorbance, otherwise absorbance Ab is the selected absorbance, if $A1a+A2a$ is to one of $A1b+A2b$ and $A1c+A2c$, then disregard all readings and proceed to step (K); or
 (J3) if the smallest absolute value of the difference between each pair of absorbances is $|(A2c-A1c)(A2a-A1a)|$, then if $A1b+A2b$ is greater than each of $A1a+A2a$ and $A1c+A2c$, compare $A1c+A2c$ and $A1a+A2a$, if $A1c+A2c< A1a+A2a$ then absorbance Ac is the selected absorbance, otherwise absorbance Aa is the selected absorbance, if $A1b+A2b$ is to one of $A1a+A2a$ and $A1c+A2c$, then disregard all readings and proceed to step (K).

26. An article of manufacture according to claim 24, wherein the predetermined fraction of the limit is 0.75 times the predetermined limit.

27. An article of manufacture according to claim 24, wherein locations a, b and c, correspond to left L, middle M and right R locations on the cuvette.

28. An article of manufacture according to claim 24, wherein prior to the step of directing at least three beams, the method further comprises:
 (i) directing at least three beams of the light at their respective different locations a, b and c on the cuvette;
 (ii) passing the at least three beams through the cuvette alone or the cuvette and sample before the sample has reacted with reagents;
 (iii) measuring at least three respective blank absorbances $A1a$, $A1b$ and $A1c$ of the transmitted beams with the detector;
 (iv) determining the sample absorbance Aa, Ab, and Ac by subtracting the blank absorbance $A1a$, $A1b$ and $A1c$ from measured sample absorbance $A2a$, $A2b$ and $A2c$ respectively.

29. An article of manufacture according to claim 25, wherein the predetermined limit is equal to intercept + slope * (minimum of $(A2a-A1a)$, $(A2b-A1b)$ or $(A2c-A1c)$), wherein the intercept and slope are determined by the analyte being measured.

30. An article of manufacture according to claim 25, wherein the predetermined absorbance is 1.0.

* * * * *